(12) United States Patent
Gebhardt et al.

(10) Patent No.: US 7,847,097 B2
(45) Date of Patent: Dec. 7, 2010

(54) METHOD FOR PRODUCTION OF 1-ALKYL-3-PHENYLURACILS

(75) Inventors: Joachim Gebhardt, Wachenheim (DE); Sandra Loehr, Ludwigshafen (DE); Michael Keil, Freinsheim (DE); Thomas Schmidt, Neustadt (DE); Jan Hendrik Wevers, Hohensuelzen (DE); Helmut Zech, Bad Duerkheim (DE); Rudolf Haeberle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/913,208

(22) PCT Filed: May 18, 2006

(86) PCT No.: PCT/EP2006/062414

§ 371 (c)(1), (2), (4) Date: Oct. 31, 2007

(87) PCT Pub. No.: WO2006/125746

PCT Pub. Date: Nov. 30, 2006

(65) Prior Publication Data

US 2008/0293941 A1  Nov. 27, 2008

(30) Foreign Application Priority Data

May 24, 2005  (DE) .................. 10 2005 024 448

(51) Int. Cl.
*C07D 239/54* (2006.01)

(52) U.S. Cl. ..................................... 544/309

(58) Field of Classification Search ................. 544/309
See application file for complete search history.

(56) References Cited

U.S. PATENT DOCUMENTS

| 4,943,309 A | 7/1990 | Bell |
| 7,375,058 B2 * | 5/2008 | Zagar et al. .............. 504/116.1 |
| 2006/0293520 A1 * | 12/2006 | Hamprecht et al. ......... 544/309 |

FOREIGN PATENT DOCUMENTS

WO  WO 01/83459 A2  11/2001

* cited by examiner

*Primary Examiner*—Venkataraman Balasubramanian
(74) *Attorney, Agent, or Firm*—Rothwell, Figg, Ernst & Manbeck, P.C.

(57) ABSTRACT

The present invention relates to a process for preparing 1-alkyl-3-phenyluracils of the formula I

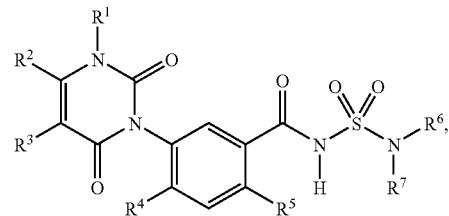

where the variables $R^1$ to $R^7$ are as defined in the description by reacting 3-phenyluracils of the formula II

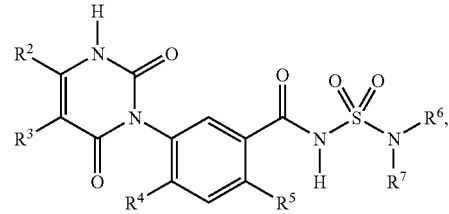

and alkylating agents of the formula III $$R^1\text{-}L^1 \qquad \qquad III,$$

with one another,
wherein during the entire reaction the pH is kept in a range from 1 to 6 by adding base a little at a time.

15 Claims, No Drawings

US 7,847,097 B2

METHOD FOR PRODUCTION OF 1-ALKYL-3-PHENYLURACILS

CROSS REFERENCE TO RELATED APPLICATION

This application is a 35 U.S.C. 371 National Phase Entry Application from PCT/EP2006/062414 filed May 18, 2006, which claims the benefit of German Patent Application No. 102005024448.3 filed on May 24, 2005, the disclosure of which is incorporated herein in its entirety by reference.

The present invention relates to a process for preparing 1-alkyl-3-phenyluracils of the formula I

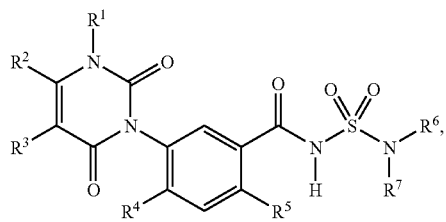

where the variables are as defined below:
$R^1$ is $C_1$-$C_6$-alkyl;
$R^2$ and $R^3$ independently of one another are hydrogen, $C_1$-$C_6$-alkyl or $C_1$-$C_6$-haloalkyl;
$R^4$ and $R^5$ independently of one another are hydrogen, halogen, cyano, $C_1$-$C_6$-alkyl or $C_1$-$C_6$-haloalkyl;
$R^6$ and $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_6$-cycloalkyl, $C_3$-$C_6$-cycloalkenyl, phenyl or benzyl;
by reacting 3-phenyluracils of the formula II

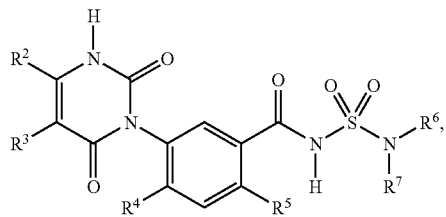

where the variables $R^2$ to $R^7$ are as defined above and alkylating agents of the formula III $$R^1\text{-}L^1 \qquad III,$$

where $R^1$ is as defined above, and
$L^1$ is halogen, hydrogensulfate, $C_1$-$C_6$-alkyl sulfate, $C_1$-$C_6$-alkyl carbonate, $C_1$-$C_6$-alkylsulfonyloxy, $C_1$-$C_6$-haloalkylsulfonyloxy or phenylsulfonyloxy,
  where the phenyl ring may carry one or more substituents from the group consisting of halogen, nitro, $C_1$-$C_6$-alkyl and $C_1$-$C_6$-haloalkyl;
wherein during the entire reaction the pH is kept in a range from 1 to 6 by adding base a little at a time.

1-Alkyl-3-phenyluracils of the general formula I are known in principle from WO 01/83459. They can be prepared as taught in WO 01/83459.

N-alkylations at the free uracil nitrogen atom by reacting a uracil compound with an alkylating agent are described, for example, in U.S. Pat. No. 4,943,309.

Furthermore, the preparation of 1-alkyl-3-phenyluracils having a sulfamide side-chain is described in PCT/EP/04/013615.

However, these procedures have the disadvantage that, owing to the fact that the sulfamide side chain can be alkylated easily, side reactions such as, for example, alkylation at the sulfonamide nitrogen atom or formation of dialkylated products occur. Correspondingly, it is already known to alkylate sulfuric acid diamides in a simple manner using sulfuric acid diesters or arenesulfonic acid esters in the presence of a base (for example R. Sowada, J. Prakt. Chem. 25, 88, 1964).

Furthermore, for trisubstituted sulfuric acid diamides, the formation of tetrasubstituted sulfuric acid diamides is known (for example B. Unterhalt, E. Seebach, Arch. Pharm. 314, 51, 1981).

It is also possible to alkylate sulfuric acid diamides where the amide function already carries an acyl radical (for example K. C. C. Bancroft et al., J. Heterocycl. Chem. 15, 1521, 1978; A. Martinez et al., Bioorg. Med. Chem. Lett. 9, 21, 3133, 1999).

Thus, it is an object of the present invention to provide a simple and economical process for preparing 1-alkyl-3-phenyluracils of the formula I which suppresses unwanted side reactions, such as, for example, the formation of dialkylated side products, and which, at the same time, allows high yields and a product of value of high purity to be obtained.

Surprisingly, it has been found that this object is achieved by a process where 3-phenyluracils of the formula II

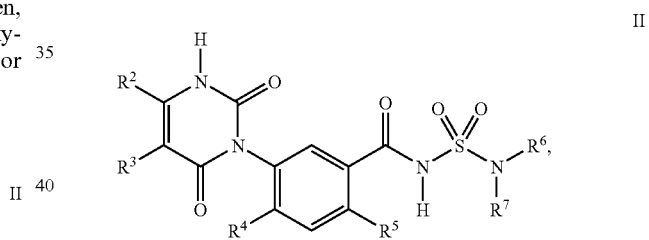

where the variables $R^2$ to $R^7$ are as defined above and alkylating agents of the formula III $$R^1\text{-}L^1 \qquad III,$$

where $R^1$ is as defined above and
$L^1$ is a nucleophilically displaceable leaving group are reacted with one another,
wherein during the entire reaction the pH is kept in a range from 1 to 6 by adding base a little at a time.

Accordingly, the present invention relates to a process for preparing 1-alkyl-3-phenyluracils of the formula I which comprises the reaction of 3-phenyluracils of the formula II and alkylating agents of the formula III, wherein during the entire reaction the pH is kept in a range from 1 to 6 by adding base a little at a time.

The process according to the invention affords 1-alkyl-3-phenyluracils of the formula I in high yields and high purities.

This is surprising with a view to the fact that the 3-phenyluracil of the formula II employed has, both at the uracil ring and in the side chain, a reactive NH group which can be alkylated.

Thus, the person skilled in the art would expect a large number of side reactions, for example the formation of corresponding N-alkylsulfonamides or mixtures of N-alkylsulfonamides or N-alkyl-substituted uracils including the formation of oligomers or polymers.

Depending on the substitution pattern, the 1-alkyl-3-phenyluracils of the formula I may contain one or more centers of chirality, in which case they are present as enantiomers or diastereomer mixtures. Thus, the invention provides a process for preparing both the pure enantiomers or diastereomers and their mixtures.

The 1-alkyl-3-phenyluracils of the formula I may also be present in the form of their agriculturally useful salts, the type of salt generally being immaterial. Suitable are, in general, the salts of those cations or the acid addition salts of those acids whose cations and anions, respectively, have no adverse effect on the herbicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogenphosphate, hydrogenphosphate, nitrate, hydrogencarbonate, carbonate, hexafluorosilicate, hexafluorophosphate, benzoate and the anions of $C_1$-$C_4$-alkanoic acids, preferably formate, acetate, propionate and butyrate.

The organic moieties mentioned for the substituents $R^1$-$R^7$ or as radicals on phenyl rings are collective terms for individual enumerations of the individual group members. All hydrocarbon chains, i.e. all alkyl, haloalkyl, alkoxy, alkenyl and alkynyl moieties, can be straight chain or branched. Unless indicated otherwise, halogenated substituents preferably carry one to five identical or different halogen atoms. Halogen means in each case fluorine, chlorine, bromine or iodine.

Examples of other meanings are:

$C_1$-$C_4$-alkyl: for example methyl, ethyl, n-propyl, 1-methylethyl, n-butyl, 1-methylpropyl, 2-methylpropyl and 1,1-dimethylethyl;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$-$C_4$-haloalkyl: a $C_1$-$C_4$-alkyl radical as mentioned above which is partially or fully substituted by fluorine, chlorine, bromine and/or iodine, i.e. for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and tridecafluorohexyl;

$C_3$-$C_7$-cycloalkyl: a monocyclic saturated hydrocarbon having 3 to 7 ring members, such as, for example, cyclopropyl, cyclobutyl, cyclopentyl, cyclohexyl or cycloheptyl;

$C_3$-$C_7$-cycloalkenyl: a monocyclic partially unsaturated hydrocarbon having 3 to 7 ring members, such as, for example, cycloprop-1-enyl, cycloprop-2-enyl, cyclobut-1-enyl, cyclobut-2-enyl, cyclobut-1,3-dienyl, cyclopent-1-enyl, cyclopent-2-enyl, cyclopent-3-enyl, cyclopent-2,4-dienyl, cyclohex-1-enyl, cyclohex-2-enyl, cyclohex-3-enyl; cyclohex-1,3-dienyl, cyclohex-1,5-dienyl, cyclohex-2,4-dienyl or cyclohex-2,5-dienyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_4$-alkoxy: for example methoxy, ethoxy, propoxy, 1-methylethoxy, butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxylbutoxy, 1,1-dimethyl-propoxy, 1,2-di-methylpropoxy, 2,2-dimethylpropoxy, 1-ethylpropoxy, hexoxy, 1-methylpentoxy, 2-methylpentoxy, 3-methylpentoxy, 4-methylpentoxy, 1,1-di-methylbutoxy, 1,2-di-methylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-tri-methylpropoxy, 1-ethyl-1-methylpropoxy and 1-ethyl-2-methylpropoxy.

In a particularly preferred embodiment of the process according to the invention, the variables $R^1$ to $R^6$ have the following meanings, in each case on their own or in combination:

$R^1$ is $C_1$-$C_4$-alkyl;
preferably methyl, ethyl, n-propyl, isopropyl;
very preferably methyl.
$R^2$ is hydrogen, $C_1$-$C_4$-alkyl or $C_1$-$C_4$-haloalkyl;
preferably hydrogen, methyl or $C_1$-$C_4$-haloalkyl;
very preferably $C_1$-$C_4$-haloalkyl;
particularly preferably difluoromethyl or trifluoromethyl;
most preferably trifluoromethyl.
$R^3$ is hydrogen, $C_1$-$C_4$-alkyl or $C_1$-$C_4$-haloalkyl;
preferably hydrogen, methyl or trifluoromethyl;
very preferably hydrogen.
$R^4$ is hydrogen or halogen;
preferably hydrogen, fluorine or chlorine;
very preferably hydrogen or fluorine;
particularly preferably fluorine.
$R^5$ is halogen, cyano or $C_1$-$C_4$-haloalkyl;
preferably fluorine, chlorine, cyano or trifluoromethyl;
also preferably halogen or cyano;
very preferably fluorine, chlorine or cyano;
particularly preferably chlorine or cyano;
most preferably chlorine.
$R^6$ is hydrogen or $C_1$-$C_4$-alkyl;
also preferably $C_1$-$C_6$-alkyl;
very preferably $C_1$-$C_4$-alkyl;
particularly preferably methyl, ethyl, n-propyl or isopropyl,
most preferably isopropyl.
$R^7$ is hydrogen or $C_1$-$C_4$-alkyl;
also preferably $C_1$-$C_6$-alkyl;
very preferably $C_1$-$C_4$-alkyl;
particularly preferably methyl, ethyl, n-propyl or isopropyl,
most preferably methyl.

In a likewise preferred embodiment of the process according to the invention, $R^2$ has the following meanings:
$R^2$ is hydrogen or $C_1$-$C_6$-haloalkyl,
preferably $C_1$-$C_6$-haloalkyl,
very preferably $C_1$-$C_4$-haloalkyl,
particularly preferably difluoromethyl or trifluoromethyl,
most preferably trifluoromethyl.

In a likewise preferred embodiment of the process according to the invention, $R^2$ has the following meanings:
$R^2$ is $C_1$-$C_6$-alkyl or $C_1$-$C_6$-haloalkyl,
preferably $C_1$-$C_4$-alkyl or $C_1$-$C_6$-haloalkyl,
very preferably $C_1$-$C_4$-haloalkyl,
particularly preferably difluoromethyl or trifluoromethyl,
most preferably trifluoromethyl.

In a likewise preferred embodiment of the process according to the invention, $R^4$ has the following meanings:
$R^4$ is hydrogen or halogen,
preferably hydrogen,
likewise preferably halogen,
very preferably fluorine or chlorine.

In a particularly preferred embodiment of the process according to the invention, 1-alkyl-3-phenyluracils of the formula I.a (corresponds to formula I where $R^2$=$CF_3$, $R^3$=H and $R^7$=$CH_3$), in particular the 1-alkyl-3-phenyluracils I.a.1 to I.a.24 of Table 1, are prepared, where the definitions of the variables $R^1$, $R^4$, $R^5$ and $R^6$ are of particular importance for the process according to the invention not only in combination with one another but in each case also on their own.

TABLE 1

I.a

[Structural formula of 1-alkyl-3-phenyluracil compound showing pyrimidine-2,4-dione ring with $R^1$ on N, $F_3C$ substituent, connected to phenyl ring with $R^4$ and $R^5$ substituents, and a sulfonamide group with $R^6$ and $CH_3$]

| No. | $R^1$ | $R^4$ | $R^5$ | $R^6$ |
|---|---|---|---|---|
| I.a.1 | $CH_3$ | H | H | $CH_3$ |
| I.a.2 | $C_2H_5$ | H | H | $CH_3$ |
| I.a.3 | $CH_3$ | F | H | $CH_3$ |
| I.a.4 | $C_2H_5$ | F | H | $CH_3$ |
| I.a.5 | $CH_3$ | H | Cl | $CH_3$ |
| I.a.6 | $C_2H_5$ | H | Cl | $CH_3$ |
| I.a.7 | $CH_3$ | F | Cl | $CH_3$ |
| I.a.8 | $C_2H_5$ | F | Cl | $CH_3$ |
| I.a.9 | $CH_3$ | H | H | $C_2H_5$ |
| I.a.10 | $C_2H_5$ | H | H | $C_2H_5$ |
| I.a.11 | $CH_3$ | F | H | $C_2H_5$ |
| I.a.12 | $C_2H_5$ | F | H | $C_2H_5$ |
| I.a.13 | $CH_3$ | H | Cl | $C_2H_5$ |
| I.a.14 | $C_2H_5$ | H | Cl | $C_2H_5$ |
| I.a.15 | $CH_3$ | F | Cl | $C_2H_5$ |
| I.a.16 | $C_2H_5$ | F | Cl | $C_2H_5$ |
| I.a.17 | $CH_3$ | H | H | $CH(CH_3)_2$ |
| I.a.18 | $C_2H_5$ | H | H | $CH(CH_3)_2$ |
| I.a.19 | $CH_3$ | F | H | $CH(CH_3)_2$ |
| I.a.20 | $C_2H_5$ | F | H | $CH(CH_3)_2$ |
| I.a.21 | $CH_3$ | H | Cl | $CH(CH_3)_2$ |
| I.a.22 | $C_2H_5$ | H | Cl | $CH(CH_3)_2$ |
| I.a.23 | $CH_3$ | F | Cl | $CH(CH_3)_2$ |
| I.a.24 | $C_2H_5$ | F | Cl | $CH(CH_3)_2$ |

The process according to the invention comprises the reaction of 3-phenyluracils of formula II and alkylating agents of the formula III wherein during the entire reaction the pH is kept in a range from 1 to 6 by adding base a little at a time:

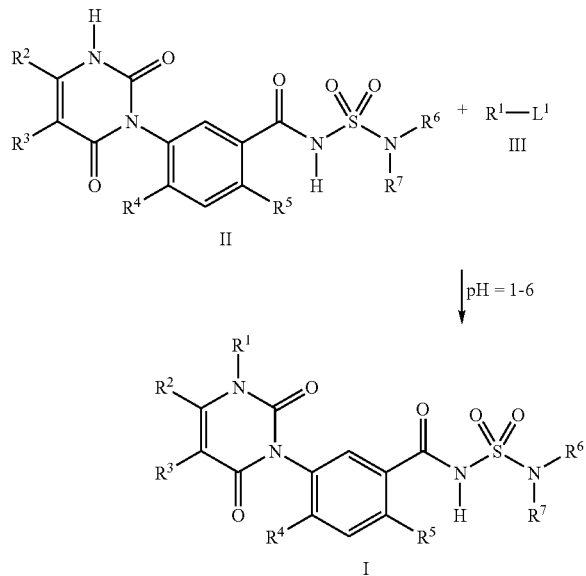

The group L$^1$ in the alkylating agent of the formula III is a nucleophilically displaceable leaving group, preferably halogen, hydrogensulfate, C$_1$-C$_6$-alkyl sulfate, C$_1$-C$_6$-alkyl carbonate, C$_1$-C$_6$-alkylsulfonyloxy, C$_1$-C$_6$-haloalkylsulfonyloxy or phenylsulfonyloxy, where the phenyl ring may carry one or more substituents from the group consisting of halogen, nitro, C$_1$-C$_6$-alkyl and C$_1$-C$_6$-haloalkyl;

very preferably halogen, C$_1$-C$_6$-alkyl sulfate, C$_1$-C$_6$-alkylsulfonyloxy, C$_1$-C$_6$-haloalkylsulfonyloxy, phenylsulfonyloxy, p-toluenesulfonyloxy, p-chlorophenyl-sulfonyloxy, p-bromophenylsulfonyloxy or p-nitrophenylsulfonyloxy;

particularly preferably halogen, C$_1$-C$_6$-alkyl sulfate, C$_1$-C$_6$-alkylsulfonyloxy, C$_1$-C$_6$-haloalkylsulfonyloxy or phenylsulfonyloxy;

very preferably C$_1$-C$_6$-alkyl sulfate;

most preferably C$_1$-C$_6$-alkyl sulfate;

also particularly preferably chlorine, bromine or iodine, methyl sulfate, methylsulfonyloxy, trifluoromethylsulfonyloxy or phenylsulfonyloxy.

3-phenyluracils of the formula II are known from WO 01/83459 and WO 04/39768 and can be prepared in accordance with the literature cited.

Preferred alkylating agents are C$_1$-C$_6$-alkyl halides, di-C$_1$-C$_6$-alkyl sulfates, di-C$_1$-C$_6$-alkyl carbonates, C$_1$-C$_6$-alkylsulfonic acids, C$_1$-C$_4$-alkyl C$_1$-C$_6$-alkyl sulfonates, C$_1$-C$_6$-haloalkylsulfonic acids, C$_1$-C$_4$-alkyl C$_1$-C$_6$-haloalkylsulfonates or C$_1$-C$_4$-alkyl phenylsulfonates, where the phenyl ring may carry one or more substituents from the group consisting of halogen, nitro, C$_1$-C$_6$-alkyl and C$_1$-C$_6$-haloalkyl.

Very preferred alkylating agents are C$_1$-C$_6$-alkyl halides, di-C$_1$-C$_6$-alkyl sulfates, C$_1$-C$_4$-alkyl C$_1$-C$_6$-alkylsulfonates or C$_1$-C$_4$-alkyl phenylsulfonates.

Likewise, very preferred alkylating agents are C$_1$-C$_6$-alkyl halides, di-C$_1$-C$_6$-alkyl sulfates, di-C$_1$-C$_6$-alkyl carbonates, C$_1$-C$_4$-alkyl C$_1$-C$_6$-alkylsulfonates or C$_1$-C$_4$-alkyl phenylsulfonates.

Particularly preferred alkylating agents are C$_1$-C$_6$-alkyl halides and di-C$_1$-C$_6$-alkyl sulfates; most preferably di-C$_1$-C$_6$-alkyl sulfates.

Likewise, particularly preferred alkylating agents are C$_1$-C$_6$-alkyl halides, di-C$_1$-C$_6$-alkyl sulfates and di-C$_1$-C$_6$-alkyl carbonates; very preferably C$_1$-C$_6$-alkyl halides and di-C$_1$-C$_6$-alkylsulfates; most preferably di-C$_1$-C$_6$-alkyl sulfates.

Particularly preferred alkylating agents are methylating agents or ethylating agents, such as methyl iodide, ethyl iodide, methyl bromide, methyl chloride, ethyl bromide, ethyl chloride, dimethyl sulfate, diethyl sulfate, methyl or ethyl C$_1$-C$_6$-alkylsulfonate or the methyl or ethyl esters of the abovementioned phenylsulfonic acids.

Likewise, especially preferred alkylating agents are methylating agents or ethylating agents, such as methyl iodide, ethyl iodide, methyl bromide, methyl chloride, ethyl bromide, ethyl chloride, dimethyl sulfate, dimethyl carbonate, diethyl sulfate, methyl or ethyl C$_1$-C$_6$-alkylsulfonates or the methyl or ethyl esters of the abovementioned phenylsulfonic acids.

A very particularly preferred methylating agent is dimethyl sulfate.

In the process according to the invention, the alkylating agent can be employed both in an equimolar amount, based on the 3-phenyluracils of the formula II, and in a substoichiometric amount or superstoichiometric amount.

Usually, at least an equimolar amount of the alkylating agent III, based on the 3-phenyluracils of the formula II is employed.

The molar ratios for the ratio of 3-phenyluracils of the formula II to alkylating agent III are generally in the range from 1:1 to 1:3, preferably from 1:1 to 1:1.3.

Suitable bases for the reaction according to the invention are all customary organic and inorganic bases.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal or alkaline earth metal fluorides, such as cesium fluoride, alkali metal amides, such as lithium amide, sodium amide and potassium amide, alkali metal and alkaline earth metal carbonates, such as lithium carbonate, sodium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example ammonia, primary amines, such as, for example, methylamine, ethylamine, hexylamine, aniline, secondary amines, such as, for example, dimethylamine, diethylamine, tertiary amines, such as trimethylamine, triethylamine, diisopropylethylamine, tributylamine, and N-methylpiperidine, pyridine, substituted pyridines, such as collidine, lutidine and 4-dimethylaminopyridine, and also bicyclic amines, such as 1,8-diazabicyclo [5.4.0]undec-7-ene (DBU), 1,5-diaza-bicyclo[4.3.0]-non-5-ene (DBN) or 1,4-diazabicyclo[2.2.2]octane (DABCO).

Preferred bases are selected from the group consisting of alkali metal and alkaline earth metal hydroxides, such as sodium hydroxide, potassium hydroxide and lithium hydroxide, alkali metal and alkaline earth metal oxides, such as calcium oxide, alkali metal and alkaline earth metal carbonates, such as lithium carbonate, sodium carbonate, potassium carbonate, cesium carbonate, magnesium carbonate, calcium carbonate, zinc carbonate, alkali metal bicarbonates, such as sodium bicarbonate and also ammonia or tertiary amines, such as triethylamine;

particularly preferably selected from the group consisting of alkali metal and alkaline earth metal hydroxides, ammonia and also tertiary amines.

Especially preferred are bases selected from the group consisting of alkali metal and alkaline earth metal hydroxides, such as sodium hydroxide, potassium hydroxide and lithium hydroxide, alkali metal and alkaline earth metal oxides, such as calcium oxide, alkali metal and alkaline earth metal carbonates, such as lithium carbonate, sodium carbonate, potassium carbonate, cesium carbonate, magnesium carbonate, calcium carbonate, zinc carbonate and also alkali metal bicarbonates, such as sodium bicarbonate.

In a particularly preferred embodiment of the process according to the invention, the base used is sodium hydroxide or potassium hydroxide, sodium carbonate or potassium carbonate or sodium bicarbonate or potassium bicarbonate.

In a very preferred embodiment of the process according to the invention, the base used is an alkali metal hydroxide or alkaline earth metal hydroxide, preferably an alkali metal hydroxide.

The bases are generally employed in equimolar amounts, based on the 3-phenyluracils of the formula II; however, they can also be employed in catalytic amounts, in excess or, if appropriate, as solvent.

Preferably, at least an equimolar amount of base, based on the compound II, is used. The amount of base is generally not more than 1.3 mol per mole of the compound II.

In the reaction according to the invention, the pH is, during the entire reaction, kept in the range from 1 to 6 by adding base a little at a time.

During the entire reaction, the pH is, by adding base a little at a time, preferably kept in a range of from 2 to 6;
very preferably from 3 to 6;
particularly preferably from 4 to 6.

"Adding base a little at a time" means that the addition of base during the reaction is in individual portions, i.e. in at least 2 portions, or in more than 2 up to many portions, or continuously.

In particular embodiments of the process according to the invention, the pH can, during the reaction, be kept by different means by adding base a little at a time in the range from 1 to 6, these embodiments being particular embodiments of the process according to the invention, both on their own and in combination:

In a preferred embodiment of the process according to the invention, at the beginning of the reaction, the pH is adjusted to between 1 and 6 and then, during the reaction, kept constant at the value adjusted at the beginning.

In a further preferred embodiment of the process according to the invention, the pH adjusted to between 1 and 6 during the beginning of the reaction is continuously changed to another pH in the range from 1 to 6 during the reaction.

In a further preferred embodiment of the process according to the invention, the continuous change of the pH during the reaction is repeated, where this repetition may be carried out as many times as desired.

In a further preferred embodiment of the process according to the invention, the pH is initially, during the beginning of the reaction, adjusted to between 1 and 6 and initially kept constant at the adjusted value. After partial reaction, this is then changed to a different pH in the range of from 1 to 6, which is then again kept constant at the newly adjusted value. This newly adjusted pH can then, after partial reaction, again be changed to a different pH in the range of from 1 to 6, i.e. the adjusted pH in the range of from 1 to 6 can, after partial reaction, be changed as many times as desired. This means that the pH adjusted to between 1 and 6 during the beginning of the reaction is changed one or more times, in each case after partial reaction, to a different pH in the range of from 1 to 6, the respective changed pH being kept constant until the next change.

In an especially preferred embodiment of the process according to the invention, the pH adjusted to between 1 and 6 during the beginning of the reaction is changed once, after partial reaction, to a different pH in the range of from 1 to 6.

Further possible preferred embodiments are all variants which are intermediate forms of the preferred embodiments mentioned above, it also hence being possible for the pH to jump to a different value in the range from 1 to 6.

All of these preferred embodiments can be combined with one another as often as desired and/or be repeated as often as desired.

The pH adjusted during the beginning of the reaction to between 1 and 6 may be higher than the pH value adjusted by the pH change or than the pH values adjusted by the pH changes.

Furthermore, the pH adjusted during the beginning of the reaction to between 1 and 6 may be lower than the pH value adjusted by the pH change or than the pH values adjusted by the pH changes.

In addition, the pH adjusted during the beginning of the reaction to between 1 and 6 may be in between the pH values adjusted by the pH changes.

Particularly preferably, the pH adjusted during the beginning of the reaction to between 1 and 6 is higher than the pH value adjusted by the pH change or than the pH values adjusted by the pH changes.

The person skilled in the art may determine the pH by standard methods, for example by periodic or continuous measurement of the pH.

For the reaction, the 3-phenyluracils of the formula II, the alkylating agents of the formula III and the base can be brought into contact in any way per se, the base being added a little at a time.

This means that the reaction partners and the base may be introduced into the reaction vessel and reacted separately, simultaneously or successively, the base being added a little at a time.

Preferably, the 3-phenyluracils of the formula II and the alkylating agents of the formula III are initially charged in a reaction vessel, if appropriate with the desired solvent, and the desired reaction conditions are then established by adding base a little at a time.

However, it is also possible to introduce into the reaction vessel the major amount or total amount of 3-phenyluracils of the formula II and the alkylating agents of the formula III, if appropriate in a solvent, and establishing the desired reaction conditions by adding base a little at a time.

The reaction of the 3-phenyluracils II with the alkylating agent III is advantageously carried out in the presence of a solvent.

Solvents suitable for these reactions are, depending on the temperature range, aliphatic, cycloaliphatic or aromatic hydrocarbons, such as pentane, hexane, cyclopentane, cyclohexane, toluene, xylene, chlorinated aliphatic and aromatic hydrocarbons, such as dichloromethane, trichloromethane, 1,2-dichloroethane, 1,1,2,2-tetrachloroethane, chlorobenzene, 1,2-,1,3- or 1,4-dichlorobenzene, chlorotoluenes, dichlorotoluenes, open-chain dialkyl ethers, such as diethyl ether, di-n-propyl ether, diisopropyl ether, methyl tert-butyl ether, cyclic ethers, such as tetrahydrofuran, 1,4-dioxane, anisole, glycol ethers, such as dimethyl glycol ether, diethyl glycol ether, diethylene glycol dimethyl ether, diethylene glycol diethyl ether, $C_1$-$C_4$-alcohols, such as methanol, ethanol, n-propanol, isopropanol, n-butanol, aliphatic $C_1$-$C_6$-alkyl carboxylates, such as methyl acetate, ethyl acetate or n-butyl acetate; ketones, such as acetone, methyl ethyl ketone, methyl isopropyl ketone, methyl isobutyl ketone, butanone, carbonates, such as diethyl carbonate and ethylene carbonate, N,N-dialkylamides, such as N,N-dimethylformamide or N,N-dimethylacetamide, N-alkyllactams, such as N-methylpyrrolidone, sulfoxides, such as dimethyl sulfoxide, tetraalkyl ureas, such as tetramethyl urea, tetraethyl urea, tetrabutyl ureas, dimethylethylene urea, dimethylpropylene urea or mixtures of these solvents.

Preferred solvents are N,N-dimethylformamide, N-methylpyrrolidone, acetone, dichloromethane, tetrahydrofuran, toluene, chlorobenzene, methyl acetate, ethyl acetate, butyl acetate or mixtures of these solvents.

Preferably, the alkylation of the 3-phenyluracils of the formula II is carried out at temperatures between −5° C. and 100° C., preferably at temperatures between 0° C. and 80° C. and in particular at temperatures between 20° C. and 70° C., very preferably between 20° C. and 60° C. The reaction time can be determined by the person skilled in the art in a manner customary per se, by standard methods, such as thin-layer chromatography or HPLC.

The reaction can be carried out at atmospheric pressure, reduced pressure or under elevated pressure, if appropriate under an inert gas, continuously or batchwise.

Work-up of the reaction mixture to obtain the 1-alkyl-3-phenyluracils of the formula I can be carried out by the methods customary for this purpose. In general, the solvent used is removed by customary processes, for example by distillation. The 1-alkyl-3-phenyluracils I can then be taken up in a water-immiscible organic solvent, any impurities are then extracted using water which, if appropriate, is acidified, the product is dried and the solvent is removed under reduced pressure. For further purification, it is possible to use customary processes such as crystallization, precipitation or chromatography.

In another variant of the process according to the invention, the reaction can also be carried out in a multiphasic system.

This variant of the process according to the invention is preferred.

With respect to alkylating agents, pH, base, temperature, pressure and work-up, what was said above applies. In general, when using a two-phase system, for work-up, the phases are separated and separately from one another worked-up by known methods.

Preferably, the reaction is carried out in an aqueous/organic multiphasic system in the presence of phase-transfer catalysts.

Examples of phase-transfer catalysts are quaternary ammonium salts, phosphonium salts, crown ethers or polyglycols.

Suitable quaternary ammonium salts comprise, for example, tetra-($C_1$-$C_{18}$)-alkylammonium fluorides, chlorides, bromides, iodides, tetrafluoroborates, diborates, hydrogensulfates, hydroxides, perchlorates and borates, such as, for example,
tetramethylammonium fluoride tetrahydrate, tetramethylammonium fluoride, tetrabutylammonium fluoride, tetrabutylammonium fluoride trihydrate, tetramethylammonium chlorine, tetraethylammonium chloride, tetrapropylammonium chloride, tetrabutylammionium chloride, dodecyltrimethylammonium chloride, methyltributylammonium chloride, methyltrioctylammonium chloride, methyltricaprylammonium chloride; tetramethylammonium bromide, tetraethylammonium chloride hydrate, tetraethylammonium bromide, tetrapropylammonium bromide (TPAB), tetrabutylammonium bromide (TEAB), tetrahexylammonium bromide, tetraoctylammonium bromide, hexadecyltrimethylammonium bromide (CTAB), dodecyltrimethylammonium bromide, tetramethylammonium bromide tetrabutylammonium iodide, tetrahexylammonium iodide, tetrabutylammonium tetrafluoroborate, $C_{12}$-$C_{14}$-trimethylammonium diborate, tetrabutylammonium hydrogensulfate (TBAHS), tetramethylammonium hydroxide (TMAOH), tetraethylammonium hydroxide, tetrapropylammonium hydroxide, tetrabutylammonium hydroxide, tetrabutylammonium perchlorate, $C_{12}$-$C_{14}$-alkyltrimethylammonium borate, $C_{12}$-$C_{14}$-alkyltrimethylammonium diborate;

N-benzyltri-($C_1$-$C_{18}$)-alkylammonium chlorides, bromides or fluorides, such as, for example,
benzyltrimethylammonium chloride (BTMAC), benzyltriethylammonium chloride (BTEAC), benzyltriethylammonium bromide, benzyltributylammonium chloride, benzyltributylammonium bromide;

phenyltri-($C_1$-$C_{18}$)-alkylammonium chlorides, bromides or fluorides, such as, for example,
phenyltrimethylammonium chloride (PTMAC);

aromatic ammonium salts, such as, for example, hexadecylpyridinium chloride,
N,N-dimethylpiperidinium hydroxide, pyridinium fluorides, chlorides or bromides, such as, for example, 1-cetylpyridinium chloride monohydrate, cetylpyridinium bromide;

preferably tetrabutylammonium chloride, methyltributylammonium chloride, methyltrioctylammonium chloride, tetrabutylammonium bromide, tetrahexylammonium bromide, tetraoctylammonium bromide, tetrabutylammonium iodide, tetrahexylammonium iodide, tetrabutylammonium hydrogensulfate and tetrabutylammonium hydroxide.

Suitable phosphonium salts comprise, for example,
$C_1$-$C_{18}$-alkyltriphenylphosphonium chlorides, bromides, acetates, such as, for example, methyltriphenylphosphonium bromide, ethyltriphenylphosphonium bromide, ethyltriphenylphosphonium iodide, ethyltriphenylphosphonium acetate, butyltriphenylphosphonium chloride, butyltriphenylphosphonium bromide,
tetra-($C_1$-$C_{18}$)-alkylphosphonium chloride or bromide, such as tetrabutylphosphonium bromide,
tetraphenylphosphonium chloride or bromide, benzyltriphenylphosphonium chloride or bromide.

Suitable crown ethers comprise, for example, 18-crown-6, dibenzo-18-crown-6.

Suitable polyglycols comprise, for example, diethyleneglycoldibutyl ether (=butyl diglyme), tetraethylene glycol dimethyl ether (=tetraglyme), triethylene glycol dimethyl ether (=triglyme), polyglycol dimethyl ether.

In general, the phase-transfer catalyst is employed in an amount of up to 20 mol %, preferably between 1 and 15 mol % and in particular between 2 and 12 mol %, based on the 3-phenyluracils II.

The multiphasic system comprises an aqueous phase and at least one organic liquid phase. In addition, solid phases may also be present.

The aqueous phase is preferably a solution of bases.

Suitable bases for this preferred variant of the process according to the invention are all customary organic and inorganic bases as mentioned above, in particular the bases mentioned above as being preferred or particularly or very preferred.

Preferred bases are alkali metal and alkaline earth metal hydroxides, such as lithium hydroxide, sodium hydroxide, potassium hydroxide and calcium hydroxide; alkali metal and alkaline earth metal carbonates, such as lithium carbonate, sodium carbonate, potassium carbonate and calcium carbonate and alkali metal bicarbonates, such as sodium bicarbonate.

Particular preference is given to using alkali metal or alkaline earth metal hydroxides, very preferably alkali metal hydroxides such as, for example, sodium hydroxide.

The bases are generally employed in equimolar amounts, based on the 3-phenyluracils of the formula II; however, they can also be employed in catalytic amounts, in excess or, if appropriate, as solvents.

Preferably, at least an equimolar amount of base, based on compound II, is employed. The amount of base is generally not more than 1.3 mol per mole of the compound II.

The aqueous phase is particularly preferably a solution of bases, such as, for example, alkali metal or alkaline earth metal hydroxides, carbonates, alkali metal bicarbonates, ammonia or water-soluble primary, secondary or tertiary amines in water.

The aqueous phase is especially preferably a solution of alkali metal or alkaline earth metal hydroxides, carbonates or alkali metal bicarbonates in water.

Preferred solvents for the organic phase are, depending on the temperature range, aliphatic, cycloaliphatic or aromatic hydrocarbons, such as pentane, hexane, cyclopentane, cyclohexane, toluene, xylene, chlorinated aliphatic and aromatic hydrocarbons, such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers, such as diethyl ether, di-n-propyl ether, diisopropyl ether, methyl tert-butyl ether, cyclic ethers, such as tetrahydrofuran (THF) and anisole, aliphatic $C_1$-$C_6$-alkyl carboxylates, such as methyl acetate, ethyl acetate or n-butyl acetate or mixtures of these solvents.

Preferred solvents for the organic phase are ethyl acetate, n-butyl acetate, chlorobenzene, THF, toluene or mixtures of these solvents; very preferred are ethyl acetate, n-butyl acetate, chlorobenzene and THF mixtures of these solvents, and also toluene and THF mixtures of toluene.

Solid phases may occur during the reaction, for example if the 1-alkyl-3-phenyluracil of the formula I, the 3-phenyluracil of the formula II, the alkylating agent of the formula III, the base and/or the phase-transfer catalyst are not fully dissolved.

In a preferred embodiment of the process according to the invention, the multiphasic system comprises, as aqueous phase, aqueous alkali metal hydroxide solution, for example, sodium hydroxide solution, and, as organic phase, toluene and tetrahydrofuran, or dichloromethane and tetrahydrofuran, chlorobenene and tetrahydrofuran, or ethyl acetate or n-butyl acetate.

For the reaction, the 3-phenyluracils of formula II, the alkylating agents of the formula III, the base and, if appropriate, the phase-transfer catalyst can be brought into contact with one another in any manner per se, the base being added a little at a time.

The reaction partners, the base and, if appropriate, the phase-transfer catalyst can be introduced into the reaction vessel and reacted separately, simultaneously or successively, the base being added a little at a time.

For example, the 3-phenyluracils of the formula II may be initially charged in one of the organic solvents or solvent mixtures mentioned above. With mixing, the aqueous solution of the base, a little at a time, the alkylating agent III and, if appropriate, the phase-transfer catalyst are then added.

Preferably, the 3-phenyluracils of the formula II and the alkylating agents of the formula III and the phase-transfer catalyst are initially charged in a reaction vessel with the desired solvent, and the desired reaction conditions are then established by adding base a little at a time.

However, it is also possible to introduce the major amount or total amount of 3-phenyluracils of the formula II and the alkylating agents of the formula III and, if appropriate, the phase-transfer catalyst, if appropriate in a solvent, into the reaction vessel, establishing the desired reaction conditions by adding base a little at a time.

The examples below serve to illustrate the invention.

Amongst other things, the ratio of desired 3-phenyluracils I to the corresponding dialkylated byproduct A was determined:

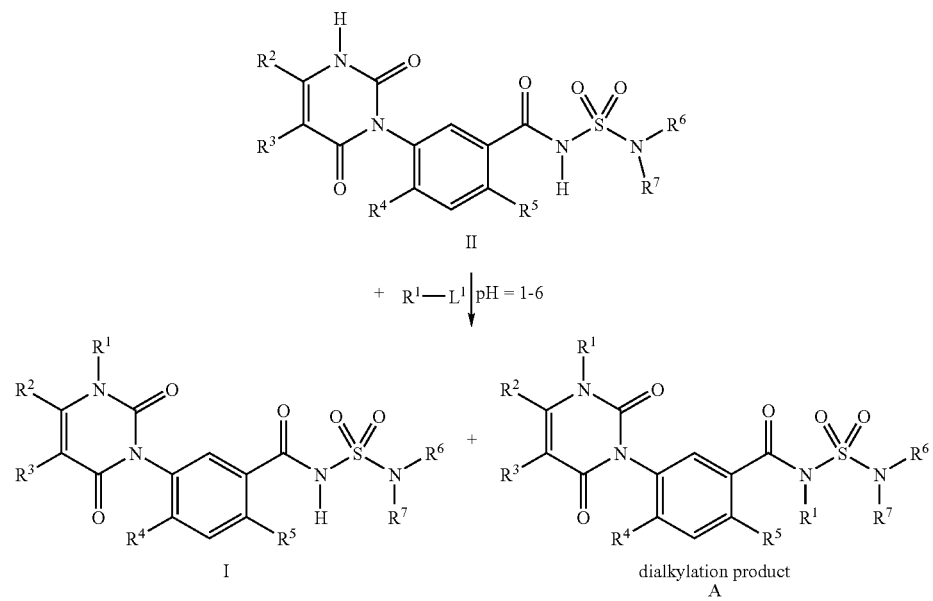

1. Reaction According to the Invention at Different Constant pH Values 12.5 g (24.5 mmol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 0.8 g (2.5 mmol) of tetrabutylammonium bromide (=TBAB) and 3.7 g (29.7 mmol) of dimethyl sulfate were initially charged in a mixture of toluene, water and THF at 25° C., and the mixture was heated to 40° C. over 6 h. By addition of aqueous 10% strength NaOH solution, the desired pH was then established in the reaction mixture.

During the entire duration of the reaction, further aqueous 10% strength NaOH solution was added, so that, during the entire course of the reaction, the pH was the pH established beforehand.

After the reaction had ended, the phases were separated, the organic phase was dried and the solvent was removed.

The yield and the ratio of desired 3-phenyluracil I to unwanted dialkylation product A were determined by quantitative HPLC (symmetry C18 5 μm for 250×4.6 mm from waters; wavelength: 205 nm; mobile phase: gradient of A (0.1% by volume of $H_3PO_4$ in $H_2O$) and B (0.1% by volume of $H_3PO_4$ in $CH_3CN$); B increasing over 25 min from 35% to 100% and then over 2 min back to 35%; flow rate: 1 ml/min) or by qualitative HPLC (Symmetry C18 5 μm 250×4.6 mm from Waters; wavelength: 220 nm; mobile phase: 40% by weight of acetonitrile/60% by weight of water/0.1% by weight of 85% strength $H_3PO_4$; flow rate: 1.5 ml/min).

The yield of 1-alkyl-3-phenyluracil I.a.23 (RT: 12.0 min; $RT_{starting\ material}$: 10.0 min) and the ratio of desired 3-phenyluracil I to unwanted dialkylation product A where $R^1=CH_3$, $R^2=CF_3$, $R^3=H$, $R^4=F$, $R^5=Cl$, $R^6=CH(CH_3)_2$, $R^7=CH_3$; hereafter "dialkylation product A.a.23" (RT: 13.4 min), at different constant pH values are shown in Table 2:

TABLE 2

| | | | Ratio [%] | |
|---|---|---|---|---|
| No. | pH | Yield [%] | 1-alkyl-3-phenyluracil I.a.23 | dialkylation product A.a.23 |
| 2.1 | 4 | 95 | 99.0 | 0.9 |
| 2.2 | 4.5 | | 99.0 | 1.1 |
| 2.3 | 5 | 94 | 98.3 | 1.6 |
| 2.4 | 5.5 | | 96.8 | 3.1 |
| 2.5 | 6 | 95 | 97.0 | 3.2 |
| 2.6 | 6.5 | 81 | 90.5 | 9.4 |
| 2.7 | 8 | 31 | 51.9 | 48.1 |

2. Reaction According to the Invention at Variable pH 40.0 g (0.0785 mol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 2.5 g (0.0078 mol) of tetrabutylammonium bromide (=TBAB) and 12.1 g (0.0957 mol) of dimethyl sulfate were initially charged in a mixture of toluene, water and THF at 25° C., and the mixture was heated at 40° C. A pH of 5.3-5.5 was then established in the reaction mixture by addition of aqueous 10% strength NaOH solution.

The mixture was stirred at 40° C. for 1 h, during which time further aqueous 10% strength NaOH solution was added, so that the pH was constant at the pH established beforehand. After 1 h, addition of the aqueous 10% strength NaOH solution was stopped, and the pH fell to 4.4-4.5. A further 0.9 g (0.0071 mol) of dimethyl sulfate was added, and the mixture was stirred for another 10 h at a pH of 4.4-4.5 and 40° C.

After the reaction had ended, the phases were separated, the organic phase was dried and the solvent was removed.

The yield and the ratio of desired 1-alkyl-3-phenyluracil I.a.23 to unwanted dialkylation product A.a.23 at variable pH were determined as mentioned under experiment 1 and are shown in Table 3:

TABLE 3

| | | | Ratio [%] | |
|---|---|---|---|---|
| No. | Reaction time [h] | Yield [%] | 1-alkyl-3-phenyluracil I.a.23 | dialkylation product A.a.23 |
| 3.1 | 1 | | 99.5 | 0.5 |
| 3.2 | 10 | 92.3 | 98.1 | 1.9 |

3. Comparative Experiment: Single Addition of Base at the Start of the Reaction 12.5 g (24.5 mmol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 0.8 g (2.5 mmol) of tetrabutylammonium bromide (=TBAB) and 3.7 g (29.7 mmol) of dimethyl sulfate and 11.6 g (2.9 mmol) of NaOH were initially charged in a mixture of toluene, water and THF at 25° C., and the mixture was heated at 40° C. over 6 h. At the beginning of the reaction, the pH was 6.3, and at the end it was 4.2.

After the reaction had ended, the phases were separated, the organic phase was dried and the solvent was removed.

The yield and the ratio of desired 1-alkyl-3-phenyluracil I.a.23 to unwanted dialkylation product A.a.23 in the case of a single addition of base at the beginning of the reaction were determined as mentioned under experiment I and are shown in Table 4:

TABLE 4

| | | Ratio [%] | |
|---|---|---|---|
| No. | Yield [%] | 1-alkyl-3-phenyluracil I.a.23 | dialkylation product A.a.23 |
| 4.1 | 91 | 94.4 | 5.5 |

4. Reaction According to the Invention Using Different Solvents 12.5 g (24.5 mmol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 0.8 g (2.5 mmol) of tetrabutylammonium bromide (=TBAB) and 3.7 g (29.7 mmol) of dimethyl sulfate were initially charged in a solvent or solvent mixture at 25° C., and the mixture was heated at 40° C. A pH of 5.3-5.5 was then established in the reaction mixture by addition of aqueous 10% strength NaOH solution.

During the entire duration of the reaction, further 10% strength NaOH solution was added so that, during the entire course of the reaction, the pH was the pH established beforehand.

After the reaction had ended, the phases were separated, the organic phase was dried and the solvent was removed.

The ratio of desired 1-alkyl-3-phenyluracil I.a.23 to unwanted dialkylation product A.a.23 for different solvents was determined as mentioned under experiment 1 and is shown in Table 5:

TABLE 5

| No. | Solvent | Reaction time [h] | Ratio [%] 1-alkyl-3-phenyluracil I.a.23 | Ratio [%] dialkylation product A.a.23 |
|---|---|---|---|---|
| 5.1 | n-butyl acetate/H$_2$O | 6 | 97.3 | 2.6 |
| 5.2 | methyl acetate/H$_2$O | 18 | 98.3 | 1.6 |
| 5.3 | ethyl acetate/H$_2$O | 23 | 97.2 | 2.8 |
| 5.4 | methylene chloride/H$_2$O | 6.5 | 95.5 | 4.5 |
| 5.5 | ethyl formate/H$_2$O | 20 | 99.4 | 0.6 |
| 5.6 | hexyl acetate/H$_2$O | 22 | 98.4 | 1.6 |
| 5.7 | DMSO/H$_2$O | 23 | 99.5 | <0.5 |
| 5.8 | 2-methyl-THF/H$_2$O | 20 | 98.1 | 1.8 |
| 5.9 | DMF/H$_2$O[1] | 41 | 92.6 | 7.4 |
| 5.10 | toluene/DMF/H$_2$O | 20 | 97.3 | 2.6 |
| 5.11 | toluene/DMF/H$_2$O | 51 | 96.7 | 3.2 |
| 5.12 | chlorobenzene/THF/H$_2$O | 18 | 94.0 | 6.0 |
| 5.13 | chlorobenzene/THF/H$_2$O | 20 | 95.0 | 5.0 |
| 5.14 | chlorobenzene/THF/H$_2$O | 32 | 97.2 | 2.8 |
| 5.15 | toluene/H$_2$O[2,3] | 22 | 91.9 | 8.1 |
| 5.16 | THF/H$_2$O[2] | 48 | 97.9 | 2.1 |

[1] without TBAB, reaction temperature 40-60° C.
[2] pH = 5.0-5.5
[3] reaction temperature = 45° C.

5. Reaction According to the Invention Using Different Alkylating Agents 12.5 g (24.5 mmol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 0.8 g (2.5 mmol) of tetrabutylammonium bromide (=TBAB) and the desired alkylating agent were initially charged in a mixture of toluene, water and THF at 25° C., and the mixture was heated at the temperature indicated. A pH of 5.3-5.5 was then established in the reaction mixture by addition of aqueous 10% strength NaOH solution.

During the entire duration of the reaction, further aqueous 10% strength NaOH solution was added so that, during the entire course of the reaction, the pH was the pH established beforehand.

After the reaction had ended, the phases were separated, the organic phase was dried and the solvent was removed.

The ratio of desired 1-alkyl-3-phenyluracil I.a.23 to unwanted dialkylation product A.a.23 for different alkylating agents was determined as mentioned under experiment 1 and is shown in Table 6:

TABLE 6

| No. | Equ. alkylating agent | Reac. cond. [h] | Reac. cond. [° C.] | Ratio [%] 1-alkyl-3-phenylur. I.a.23 | Ratio [%] dialkyl. prod. A.a.23 |
|---|---|---|---|---|---|
| 6.1 | 1.2 equ. dimethyl sulfate | 6 | 40 | 96.8 | 3.1 |
| 6.2 | 1.5 equ. methyl iodide[1] | 6 | 40 | 96.2 | 3.8 |
| 6.3 | 1.5 equ. methyl iodide | 27 | 40-70 | 94.9 | 5.1 |
| 6.4 | 1.2 equ. (H$_3$CO)$_2$CO$_2$ | 36 | 125 | 100 | 0 |

[1] Solvent = DMF/H$_2$O

6. Reaction According to the Invention Using Different Phase-Transfer Catalysts 125 g (0.24 mol) 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, (0.02 mol) of phase-transfer catalyst and 37 g (0.30 mol) of dimethyl sulfate were initially charged in a mixture of toluene, water and THF at 25° C., and the mixture was heated at 40° C. A pH of 5.0-5.5 was then established in the reaction mixture by addition of aqueous 10% strength NaOH solution.

During the entire duration of the reaction, further aqueous 10% strength NaOH solution was added so that, during the entire course of the reaction, the pH was the pH established beforehand.

After the reaction had ended, the phases were then separated, the organic phase was dried and the solvent was removed.

The ratio of desired 1-alkyl-3-phenyluracil I.a.23 to unwanted dialkylation product A.a.23 for different phase-transfer catalysts was determined as mentioned under experiment 1 and is shown in Table 7:

TABLE 7

| No. | Phase-transfer catalyst | Reaction time [h] | Ratio [%] 1-alkyl-3-phenylur. I.a.23 | Ratio [%] dial. A.a.23 |
|---|---|---|---|---|
| 7.1 | tetrabutylammonium chloride | 3 | 98.7 | 1.3 |
| 7.2 | tetrabutylammonium chloride | 6 | 97.8 | 2.2 |
| 7.3 | tetrabutylammonium bromide | 3 | 98.6 | 1.4 |
| 7.4 | tetrabutylammonium bromide | 6 | 97.5 | 2.5 |
| 7.5 | tetrabutylammonium hydroxide | 3 | 96.8 | 3.2 |
| 7.6 | tetrabutylammonium hydroxide | 6 | 95.1 | 4.9 |
| 7.7 | tetrabutylammonium hydrogensulfate | 3 | 97.7 | 2.2 |
| 7.8 | tetrabutylammonium hydrogensulfate | 6 | 94.0 | 6.0 |
| 7.9 | tetrahexylammonium bromide | 3 | 96.9 | 3.1 |
| 7.10 | tetrahexylammonium bromide | 6 | 96.2 | 3.8 |
| 7.11 | methyltrioctylammonium chloride | 3 | 97.3 | 2.7 |
| 7.12 | methyltrioctylammonium chloride | 6 | 95.8 | 4.0 |

7. Reaction According to the Invention at Different Reaction Temperatures 12.5 g (24.5 mmol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 0.8 g (2.5 mmol) of tetrabutylammonium bromide (=TBAB) and 3.7 g (29.7 mmol) of dimethyl sulfate were initially charged in a mixture of toluene, water and THF at 25° C., and the mixture was heated at the stated temperature. A pH of 5.3-5.4 was then established in the reaction mixture by addition of aqueous 10% strength NaOH solution.

During the entire duration of the reaction, further aqueous 10% strength NaOH solution was added so that, during the entire course of the reaction, the pH was the pH established beforehand.

After the reaction had ended, the phases were separated, the organic phase was dried and the solvent was removed.

The yield and the ratio of desired 1-alkyl-3-phenyluracil I.a.23 to unwanted dialkylation product A.a.23 were determined as mentioned under experiment 1 and are shown in Table 8:

TABLE 8

| | | | Ratio [%] | |
|---|---|---|---|---|
| No. | Temp. [° C.] | Yield [%] | 1-alkyl-3-phenyluracil I.a.23 | dialkylation product A.a.23 |
| 8.1 | 30 | 89 | 99.0 | 1.0 |
| 8.2 | 50 | 89 | 98.7 | 1.3 |
| 8.3 | 60 | 86 | 98.4 | 1.6 |
| 8.4 | 70 | 54 | 99.3 | 0.7 |

8. Variation of the Addition of the Methylating Agent

8a. Addition of the Methylating Agent at the Beginning of the Reaction 50.0 g (0.98 mol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 3.2 g (0.0089 mol) of tetrabutylammonium bromide (=TBAB) and 15.1 g (0.12 mol) of dimethyl sulfate were initially charged in a mixture of toluene, water and THF at 25° C., and the mixture was heated at 40° C. A pH of 5.3-5.5 was then established in the reaction mixture by addition of aqueous 10% strength NaOH solution.

During the entire duration of the reaction, further aqueous 10% strength NaOH solution was added so that, during the entire course of the reaction, the pH was the pH established beforehand.

After the reaction had ended, the phases were separated, the organic phase was dried and the solvent was removed.

The ratio of desired 1-alkyl-3-phenyluracil I.a.23 to unwanted dialkylation product A.a.23 was determined as mentioned under experiment 1 and is shown in Table 9:

TABLE 9

| | | Ratio [%] | |
|---|---|---|---|
| No. | Reaction time [h] | 1-alkyl-3-phenyluracil I.a.23 | dialkylation product A.a.23 |
| 9.1 | 0 | 0 | 0 |
| 9.2 | 0.5 | 99.4 | 0.6 |
| 9.3 | 1 | 99.4 | 0.6 |
| 9.4 | 1.5 | 99.0 | 0.9 |
| 9.5 | 2 | 98.3 | 1.7 |
| 9.6 | 2.5 | 97.5 | 2.5 |
| 9.7 | 3 | 97.0 | 3.0 |
| 9.8 | 3.5 | 97.0 | 3.0 |

8b. Addition of the Methylating Agent a Little at a Time During the Reaction 70.0 g (0.1321 mol) of 2-chloro-5-[3,6-dihydro-2,6-dioxo-4-(trifluoromethyl)-1(2H)-pyrimidynyl]-4-fluoro-N-{[methyl-(1-methylethyl)amino]sulfonyl}benzamide, 4.3 g (0.0132 mol) of tetrabutylammonium bromide (=TBAB) were initially charged in a mixture of toluene, water and THF at 25° C., and the mixture was heated at 40° C. A pH of 5.3-5.5 was then established in the reaction mixture by addition of aqueous 10% strength NaOH solution.

During the entire duration of the reaction, further aqueous 10% strength NaOH solution was added so that, during the entire course of the reaction, the pH was the pH established beforehand.

21.0 g (0.17 mol) of dimethyl sulfate in toluene were added dropwise over a period of 8 h.

After the reaction had ended, the phases were separated, the organic phase was dried and the solvent was removed.

The ratio of desired 1-alkyl-3-phenyluracil I.a.23 to unwanted dialkylation product A.a.23 was determined as mentioned under experiment 1 and is shown in Table 10:

TABLE 10

| | | Ratio [%] | |
|---|---|---|---|
| No. | Reaction time [h] | 1-alkyl-3-phenyluracil I.a.23 | dialkylation product A.a.23 |
| 10.1 | 8 | 99.0 | 1.0 |
| 10.2 | 12 | 96.9 | 3.0 |

9. Reaction According to the Invention With Various Bases

At 25° C., 35.0 g (68.6 mmol) of 2-chloro-5-[3,6-dihydro-2,6-dioxo-4-(trifluoromethyl)-1(2H)-pyrimidinyl]-4-fluoro-N-{[methyl-(1-methylethyl)amino]sulfonyl}benzamide, 2.2 g (6.9 mmol) of tetrabutylammonium bromide (=TBAB) and 10.6 g (85.1 mmol) of dimethyl sulfate were initially charged in a solvent or solvent mixture, and the mixture was warmed to 40° C. By addition of 10% strength aqueous solution of the base, the pH of the reaction mixture was then adjusted to 5.3-5.5. During the entire reaction time, more 10% strength aqueous solution of the base was added, so that during the entire course of the reaction the pH was constant at the pH adjusted beforehand.

After 4 h, the phases were separated, the organic phase was dried and the solvent was removed.

The ratio of desired 1-alkyl-3-phenyluracil I.a.23 to unwanted dialkylation product A.a.23 for the practice of the reaction with various bases was determined as mentioned under experiment 1 and is shown in Table 11:

TABLE 11

| | | | Ratio [%] | |
|---|---|---|---|---|
| No. | Base | Yield [%] | 1-alkyl-3-phenyluracil I.a.23 | dialkylation product A.a.23 |
| 11.1 | LiOH | 91.8 | 99.6 | 3.4 |
| 11.2 | NaOH | 91.9 | 97.2 | 2.8 |
| 11.3 | KOH | 92.5 | 97.4 | 2.6 |
| 11.4 | NH$_3$ | 90.5 | 96.8 | 3.2 |
| 11.5 | N(C$_2$H$_5$)$_3$* | | 98.4 | 1.6 |
| 11.6 | DABCO | | 99.6 | 0.4 |

*the pH was adjusted by addition of 5% strength aqueous solution

We claim:

1. A process for preparing a 1-alkyl-3-phenyluracil of the formula I

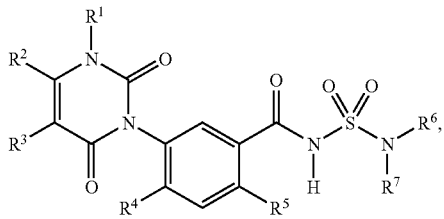

or a herbicidally acceptable salt thereof,
where the variables are as defined below:
$R^1$ is $C_1$-$C_6$-alkyl;
$R^2$ and $R^3$ independently of one another are hydrogen, $C_1$-$C_6$-alkyl or $C_1$-$C_6$-haloalkyl;
$R^4$ and $R^5$ independently of one another are hydrogen, halogen, cyano, $C_1$-$C_6$-alkyl or $C_1$-$C_6$-haloalkyl;
$R^6$ and $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_6$-cycloalkyl, $C_3$-$C_6$-cycloalkenyl, phenyl or benzyl;
comprising reacting a 3-phenyluracil of the formula II

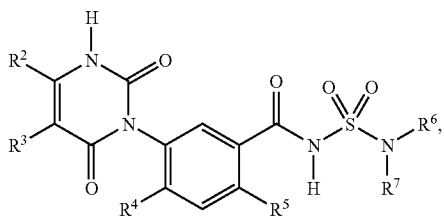

or a herbicidally acceptable salt thereof,
where the variables $R^2$ to $R^7$ are as defined above
with an alkylating agent of the formula III $$R^1\text{-}L^1 \qquad \qquad \text{III,}$$

where $R^1$ is as defined above and
$L^1$ is halogen, hydrogensulfate, $C_1$-$C_6$-alkyl sulfate, $C_1$-$C_6$-alkyl carbonate, $C_1$-$C_6$-alkylsulfonyloxy, $C_1$-$C_6$-haloalkylsulfonyloxy or phenylsulfonyloxy,
where the phenyl ring may carry one or more substituents selected from the group consisting of halogen, nitro, $C_1$-$C_6$-alkyl and $C_1$-$C_6$-haloalkyl,
wherein during the entire reaction the pH is kept in a range from 1 to 6 by adding base a little at a time.

2. The process for preparing a 1-alkyl-3-phenyluracil of the formula I according to claim 1, wherein the alkylating agent is selected from the group consisting of $C_1$-$C_6$-alkyl halides, di-$C_1$-$C_6$-alkyl sulfates, $C_1$-$C_6$-alkyl $C_1$-$C_4$-alkylsulfonates and $C_1$-$C_4$-alkyl phenylsulfonates.

3. The process for preparing a 1-alkyl-3-phenyluracil of the formula I according to claim 1, wherein the alkylating agent is a di-$C_1$-$C_6$-alkyl sulfate.

4. The process for preparing a 1-alkyl-3-phenyluracil of the formula I according to claim 1, wherein during the entire reaction the pH is kept in a range from 3 to 6 by adding base a little at a time.

5. The process for preparing a 1-alkyl-3-phenyluracil of formula I according to claim 1, wherein at the start of the reaction the pH is adjusted to between 1 and 6 and then during the reaction kept constant at the value adjusted at the beginning.

6. The process for preparing a 1-alkyl-3-phenyluracil of the formula I according to claim 1, wherein the pH is adjusted during the beginning of the reaction to a value between 1 and 6, and is during the reaction changed continuously to another pH in the range of from 1 to 6.

7. The process for preparing a 1-alkyl-3-phenyluracil of the formula I according to claim 1, wherein the pH is adjusted constantly during the beginning of the reaction to a value between 1 and 6, and is changed once or more than once, in each case after partial reaction, to another pH in the range of from 1 to 6, the respective changed pH being kept constant until the next change.

8. The process for preparing a 1-alkyl-3-phenyluracil of the formula I according to claim 1, wherein the reaction is carried out in an aqueous/organic multiphase system in the presence of at least one phase-transfer catalyst.

9. The process for preparing a 1-alkyl-3-phenyluracil of the formula I according to claim 8, wherein the phase-transfer catalyst is selected from the group consisting of quaternary ammonium salts, phosphonium salts, crown ethers and polyglycols.

10. The process for preparing a 1-alkyl-3-phenyluracil of the formula I according to claim 8, wherein the aqueous phase is a solution of at least one alkali metal or alkaline earth metal hydroxide, carbonate or alkali metal bicarbonate in water.

11. The process for preparing a 1-alkyl-3-phenyluracil of the formula I according to claim 1, wherein
$R^2$ is $C_1$-$C_4$-haloalkyl;
$R^3$ is hydrogen;
$R^4$ is hydrogen or fluorine;
$R^5$ is chlorine and
$R^6$ and $R^7$ are $C_1$-$C_6$-alkyl.

12. The process of claim 11, wherein $R^1$ is methyl.

13. The process of claim 1, wherein $R^2$ is hydrogen or $C_1$-$C_6$-haloalkyl.

14. The process of claim 1, wherein $R^2$ is $C_1$-$C_6$-alkyl or $C_1$-$C_6$-haloalkyl.

15. The process of claim 1, wherein $R^4$ is hydrogen or halogen.

* * * * *